United States Patent [19]
Branson

[11] Patent Number: 5,993,397
[45] Date of Patent: Nov. 30, 1999

[54] INFANT RESPIRATORY MONITOR

[76] Inventor: Krista Lynn Branson, 5546 Horseshoe Way, Fontana, Calif. 92336

[21] Appl. No.: 09/012,626

[22] Filed: Jan. 23, 1998

[51] Int. Cl.⁶ ..................................... A61N 5/00
[52] U.S. Cl. ......................... 600/534; 600/386; 600/300; 600/529
[58] Field of Search .................................. 600/500–503, 600/532–538, 595, 386–391, 534, 504, 529, 481–486, 300–301; 128/897–899; 340/573.1

[56] References Cited

U.S. PATENT DOCUMENTS

| | | | |
|---|---|---|---|
| 5,400,012 | 3/1995 | Walton | 600/534 |
| 5,423,328 | 6/1995 | Gavish | 600/534 |
| 5,454,376 | 10/1995 | Stephens et al. | 600/534 |

*Primary Examiner*—Cary O'Connor
*Assistant Examiner*—Michael Astorino
*Attorney, Agent, or Firm*—Goldstein & Canino

[57] ABSTRACT

An infant respiratory monitor for alerting the supervisors of an infant when there is a lack of movement of the infant due to potential respiratory problems. The device comprises a housing having an attachment for clip for securing the housing to an infant. Respiratory monitoring circuitry is contained within the housing, and comprises a power source which is in circuit with a motion sensor, processor and audio output means. The motion sensor detects movement, and transmits the presence of such movement to the processor. The processor is configured to count the number of signals received from the motion sensor within a pre-determined time period and alert the sound output means in the event that the number of signals received within the pre-determined period of time from the motion sensor drops below a pre-determined value. Upon that occurrence, the processor signals the audio output means to emit an audible alert warning noise.

4 Claims, 2 Drawing Sheets

INFANT RESPIRATORY MONITOR

FIELD OF THE INVENTION

The invention relates to an infant respiratory monitor. More particularly, the invention relates to a device which may be secured to an infant to safely monitor the breathing of said infant and sound an audible alarm in the event of a cessation of the infant's breathing longer than a pre-determined period of time.

BACKGROUND OF THE INVENTION

The risks inherent in leaving infants unattended for even short lengths of time are well known. In addition to the harm which infants can cause to themselves upon being left unattended, they can also suffer harm due to such things as "sudden infant death syndrome", "crib death" and numerous other vague maladies which all too often cause death to an infant. While various monitoring devices are well known in the art which attempt to monitor an unattended infant by detecting the infant's screams or cries (such as traditional intercom systems), these devices fail to signal an alert unless the infant audibly signals that he or she is uncomfortable (i.e. by crying).

Quite commonly, unattended infants suffer from maladies which do not result in the infant crying, and hence would not tend to alert the infant's absent parents or supervisors. Sudden infant death syndrome (or SIDS) for example, results in the death of an infant without any noticeable discomfort or pain to the infant. Accordingly, children afflicted with SIDS can simply pass from a sleeping phase into a non-respiratory near-death situation without any notice. The only manner of safeguarding against such a situation would be to directly monitor the respiration of the infant to ensure that said respiration is regular and uninterrupted.

Consequently, even infants under direct supervision are at risk from certain maladies such as SIDS unless their respiratory pattern is directly monitored. For that reason, a device or apparatus is needed in the art which attempts not to detect audible cries or screams from an infant, but rather monitors the respiratory pattern of the infant and provides an alert in response to any observable irregularities thereof. Such a device would be employable and useful for an infant which is unattended (such as in a separate room from his or her parents or keeper) and even for infants which are under supervision but sleeping.

While the traditional prior art units such as audible infant intercom monitors may be suitable for the particular purpose employed, or for general use, they would not be as suitable for the purposes of the present invention as disclosed hereafter.

SUMMARY OF THE INVENTION

The present invention relates to a device which may be secured to an infant to safely monitor the breathing of said infant and sound an audible alarm in the event of a cessation of the infant's breathing longer than a pre-determined period of time.

In accordance with the invention, there is provided an infant respiratory monitor which can monitor the respiratory patterns of an infant and sound an alert in response to any defined irregularities thereof.

Further in accordance with the invention, there is provided an infant respiratory monitor which is useful in monitoring an unattended infant as well as a supervised but sleeping infant.

Further in accordance with the invention, there is provided an infant respiratory monitor which is light-weight and capable of being safely and comfortably secured to an infant without encumbering, irritating or harming the infant.

Further in accordance with the invention, there is provided an infant respiratory monitor which utilizes only low-voltage electrical circuitry, and thus presents no possible threat of electrical shock to the infant upon whom the device is employed.

Further and finally in accordance with the invention, here is provided an infant respiratory monitor which is inexpensive and simple to manufacture, said monitoring device consisting merely of simple electrical components encased within a non-toxic plastic housing.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
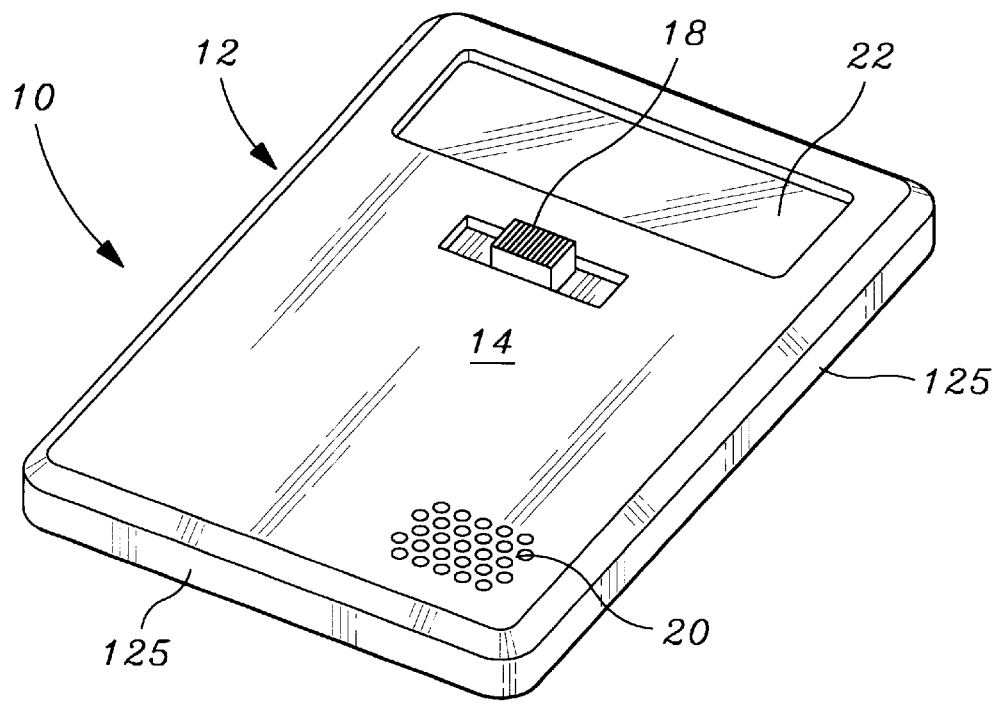
FIG. 1 is a diagrammatic perspective view of the front surface of the infant respiratory monitor of the instant invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the infant respiratory monitor. The words "proximal end" and "distal end" refer, respectively, to ends of an object nearer to and further from the operator of the object when the object is used in a normal fashion or as is described in the specification.

FIG. 1 illustrates an infant respiratory monitor 10 of the instant invention. The infant respiratory monitor 10 comprises a housing 12, preferably constructed of high-impact plastic but also potentially constructed of any other suitable material known to those skilled in the art. As seen by also referring to FIG. 2, the housing 12 consists of a front surface 14 and opposite rear surface 16. At least one side 125 co-joins the front surface 14 and rear surface 16. While the shape of the housing 12 which is shown in the drawings is rectangular and hence results in the presence of four distinct sides 125, it is also envisioned that the housing can take any other suitable shape, including round.

A switch 18 is shown located upon the front surface 14 of the housing 12 of the infant respiratory monitor 10, the witch 18 capable of activating the infant respiratory monitor 10. It is further envisioned that the switch 18 may be located upon the rear surface 16 of the housing 12, or upon one of the sides 12S. Sound output means 20 are also shown located upon the front surface 14 of the housing 12 of the infant respiratory monitor 10, but may also preferably be located upon the rear surface 16 or one of the sides 12S (to avoid being muffled when pressed against the infant or the infant's bed sheets, for instance). In addition, information display means such as a liquid crystal display (LCD) 22 are also disposed upon the housing 12 for conveying certain desired information.

Figure 2:
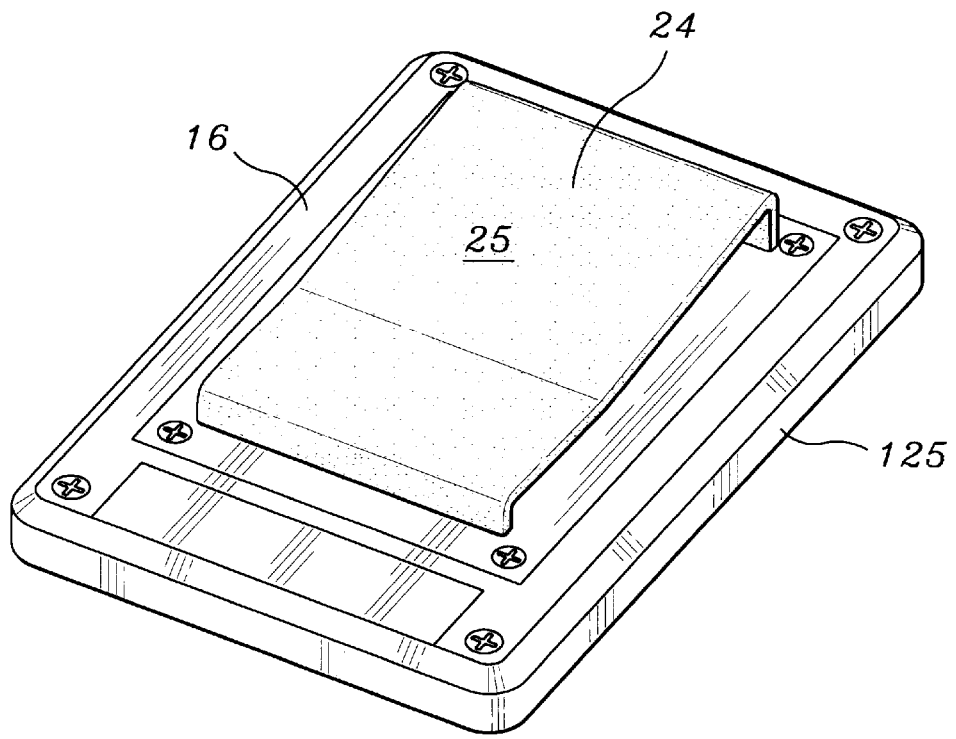
FIG. 2 is a diagrammatic perspective view of the rear surface and securing clip of the infant respiratory monitor of the instant invention.
Figure 3:
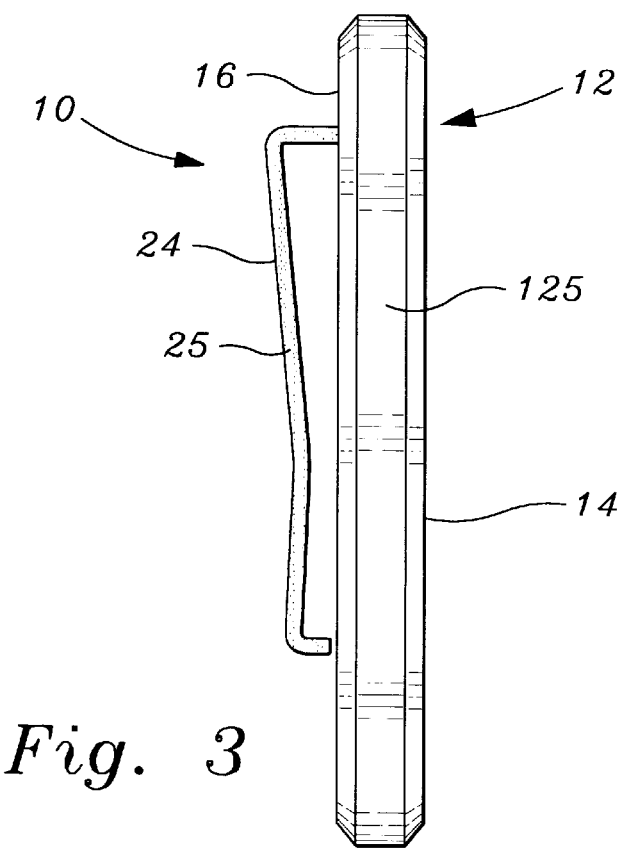
FIG. 3 is a side view of the infant respiratory monitor of the instant invention.

Attachment means, such as the attachment clip 24 seen in FIG. 2 and FIG. 3 are located upon the housing 12 of the infant respiratory monitor 10. The attachment clip 24 shown is covered with a soft foam-like material 25 to avoid the possibility of injuring or irritating the infant. It is envisioned that the monitor 10 be secured to the infant by securing the attachment clip 24 to the infant's diaper or related garment. When attached thereto, the monitor 10 will be capable of monitoring the respiratory pattern of the infant by sensing movement of the infant as his or her abdomen/chest moves due to normal respiration. The monitor 10 is configured to convey an alert in the event that a lack of movement (i.e. lack of respiration) occurs for a pre-determined interval of time. The circuitry which enables this is described in detail below.

Figure 4:
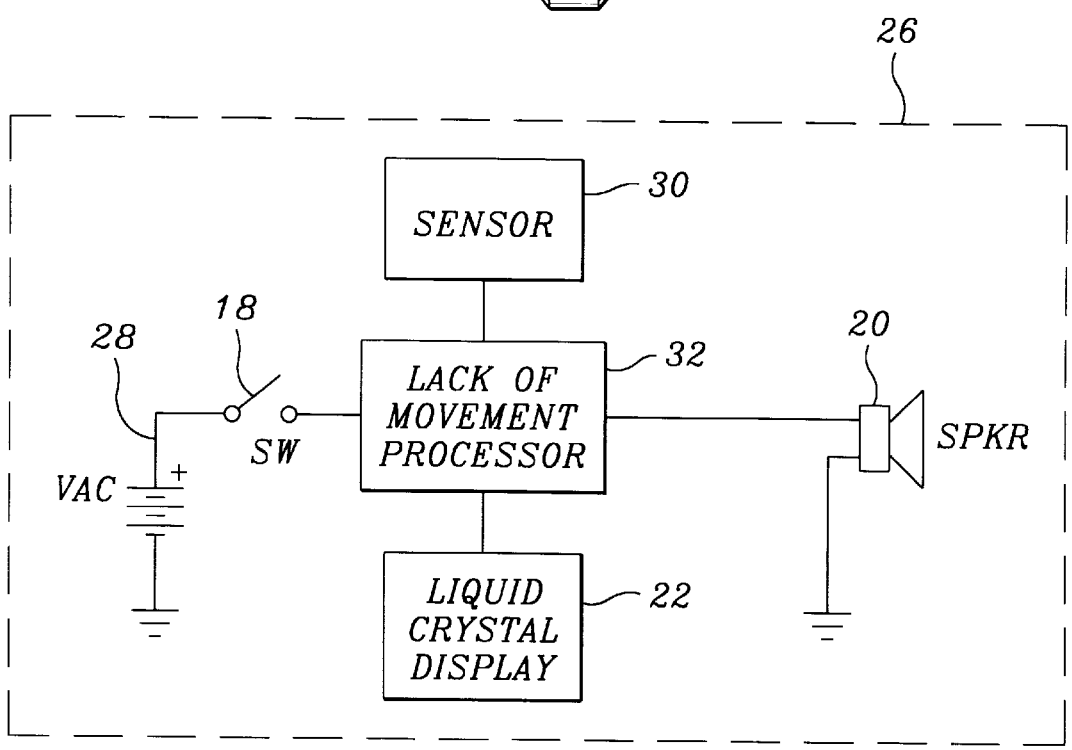
FIG. 4 is a block diagram which illustrates the operation of the respiratory monitoring circuitry of the instant invention.

Located within the housing 12 of the infant respiratory monitor 10 is respiratory monitoring circuitry 26 as depicted in FIG. 4. The circuitry 26 consists of a power source 28 which is in electrical circuit (by way of standard electrical wires or the like) with a motion sensor 30, a processor 32, the information display means 22 as mentioned earlier, and the sound output means 20 as also mentioned earlier. The electrical path between the power source 28 and the remaining components of the circuitry 26 is interrupted by the switch 18 which allows the path to be selectively opened or closed. To activate the infant respiratory monitor 10, the switch 18 is closed, and thus current is permitted to flow from the power source 28 to the remainder of the circuitry 26.

The motion sensor 30 of the respiratory monitoring circuitry 26 is of the type which are well known to those skilled in the art, and capable of detecting motion of the sensor 30 itself upon the device 10 being activated (i.e. upon the switch being closed and current permitted to flow from the power source to the components of the circuit 26). Each time the motion sensor 30 detects movement, a signal is transmitted to the processor 32 which is in circuit with the motion sensor 30. The processor 32 is configured to count the number of signals received from the motion sensor 30 within a pre-determined time period, and alert the sound output means 20 in the event that the number of signals received within the pre-determined period of time from the motion sensor 30 drops below a pre-determined value. Upon being alerted by the processor 32, the sound output means 20 will emit an audible alert warning noise.

Accordingly, a cessation in the infant's respiration will cause the processor to alert the sound output means 20, and an audible alert will be emitted therefrom to warn the infant's supervisors of a potential problem with the infant's breathing. The infant's supervisors may then check on the infant and take appropriate action. The information display means such as the liquid crystal display 22 (LCD) may be configured to receive certain processed information from the processor 32 such as the number of movements (i.e. breathing cycles) detected over a certain time, and relay said information to the infant's supervisor.

What is claimed is:

1. An infant respiratory monitor for alerting the supervisors of an infant when there is a lack of movement of the infant due to potential respiratory problems; comprising:

a) a housing, the housing having a front surface, a rear surface and at least one side which co-joins the front surface and the rear surface;

b) an attachment clip located upon the housing for securing the housing to an infant; and c) respiratory monitoring circuitry located within the housing, said circuitry comprising a power source which is in electrical circuit with a motion sensor as well as a processor and sound output means, a switch disposed between the power source and remaining circuitry components, the switch capable of completing an electrical connection between said power source and remaining circuitry components when the infant respiratory monitor is intended to be activated, wherein the motion sensor of the activated infant respiratory monitor which is secured to the infant transmits a signal to the processor each time movement of the infant is detected by said motion sensor, and the processor is configured to count the number of signals received from the motion sensor within a pre-determined time period and alert the sound output means in the event that the number of signals received within the pre-determined period of time from the motion sensor drops below a pre-determined value, in which case the processor will signal the audio output means to emit an audible alert warning noise.

2. The infant respiratory monitor of claim one, wherein the attachment clip is encased in a soft foam-like material to avoid the possibility of injuring or irritating the infant when the device is secured to the infant.

3. The infant respiratory monitor of claim two, further comprising information display means such as a liquid crystal display which is in circuit with the processor and disposed upon the housing, said display means capable of conveying certain desired information from the processor to a user.

4. The infant respiratory monitor of claim three, wherein the switch of the respiratory monitoring circuitry is accessible through the housing so that the user may selectively activate or de-activate said monitor.

* * * * *